(12) United States Patent
Errante et al.

(10) Patent No.: US 12,428,444 B2
(45) Date of Patent: Sep. 30, 2025

(54) BIOACTIVE PEPTIDES AND COMPOSITIONS COMPRISING THEM

(71) Applicants: ESPIKEM S.R.L., Prato (IT); UNIVERSITA DEGLI STUDI DI FIRENZE, Florence (IT)

(72) Inventors: Fosca Errante, Prato (IT); Lisa Giovannelli, Fiesole (IT); Anna Maria Papini, Florence (IT); Paolo Rovero, Florence (IT)

(73) Assignees: ESPIKEM S.R.L., Prato (IT); UNIVERSITA DEGLI STUDI DI FIRENZE, Florence (IT)

( * ) Notice: Subject to any disclaimer, the term of this patent is extended or adjusted under 35 U.S.C. 154(b) by 902 days.

(21) Appl. No.: 17/615,201

(22) PCT Filed: Jun. 5, 2020

(86) PCT No.: PCT/IB2020/055291
§ 371 (c)(1),
(2) Date: Nov. 30, 2021

(87) PCT Pub. No.: WO2020/245772
PCT Pub. Date: Dec. 10, 2020

(65) Prior Publication Data
US 2022/0227807 A1    Jul. 21, 2022

(30) Foreign Application Priority Data
Jun. 7, 2019   (IT) .................. 102019000008364

(51) Int. Cl.
| C07K 5/113 | (2006.01) |
| A61K 8/64 | (2006.01) |
| A61P 17/00 | (2006.01) |
| A61Q 19/08 | (2006.01) |
| A61K 38/00 | (2006.01) |

(52) U.S. Cl.
CPC .............. *C07K 5/1021* (2013.01); *A61K 8/64* (2013.01); *A61P 17/00* (2018.01); *A61Q 19/08* (2013.01); *A61K 38/00* (2013.01); *A61K 2800/782* (2013.01)

(58) Field of Classification Search
CPC .......... C07K 5/1021; C07K 1/04; A61K 8/64; A61K 38/00; A61K 2800/782; A61P 17/00; A61P 17/02; A61Q 19/08
See application file for complete search history.

(56) References Cited

U.S. PATENT DOCUMENTS 5,763,576 A    6/1998  Powers

FOREIGN PATENT DOCUMENTS

CN         104211769 A   * 12/2014

OTHER PUBLICATIONS

CN104211769A Google ENglish Translation of Description and Claims, accessed on Sep. 18, 2024.*
Andrea Groß, Eichler J (2016) Synthetic Peptides as Protein Mimics. Synthetic Peptides as Protein Mimics Front. Bioeng. Biotechnol. 3:211.*
Thermofischer, Technical Information, N-Terminal Acetylation and C-Terminal Amidation of Peptides, publsihed online 2004.*
Koushik Chandra, A highly efficient in situ N-acetylation approach for solid phase synthesis, Org. Biomol. Chem., 2014, 12, 1879-1884 | 1879.*
Cipriani et al., "Serpin A 1 and the modulation of type I collagen turnover: Effect of the C-terminal peptide 409-418 (SA1-111) in human dermal fibroblasts", Cell Biol Int, 2018, vol. 42, No. 10, pp. 1340-1348.
International Search Report and Written Opinion for Corresponding International Application No. PCT/IB2020/055291 (12 Pages) (Nov. 11, 2020).

* cited by examiner

*Primary Examiner* — Lianko G Garyu
*Assistant Examiner* — Erinne R Dabkowski
(74) *Attorney, Agent, or Firm* — LUCAS & MERCANTI, LLP

(57) ABSTRACT

The present invention relates to bioactive peptides and to the cosmeceutical compositions containing them, useful for the prevention and treatment of the signs of skin aging, such as wrinkles, fine lines and loss of firmness and elasticity of the skin, thanks to their efficacy in the protection of the dermal collagen.

11 Claims, 1 Drawing Sheet
Specification includes a Sequence Listing.

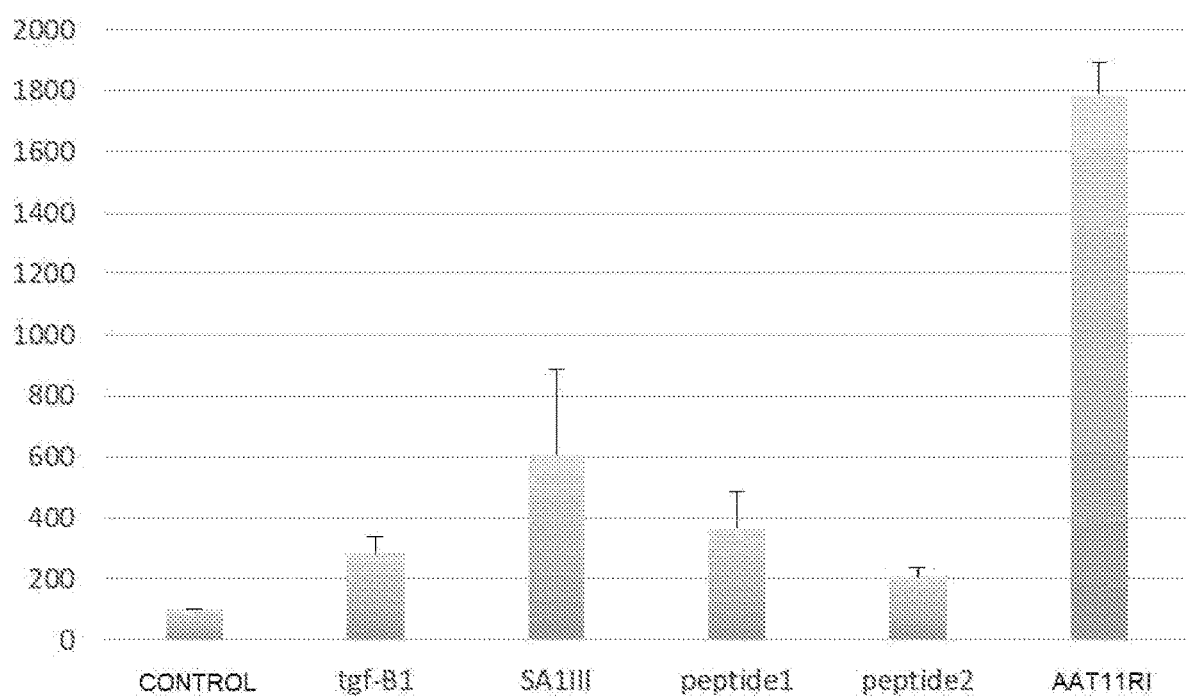

SEQUENCE LISTING

```
<160> NUMBER OF SEQ ID NOS: 5

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1

Asn Val Val Lys
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide

<400> SEQUENCE: 2

Asn Val Val Lys
1

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide

<400> SEQUENCE: 3

Met Gly Lys Val Val Asn Pro Thr Gln Lys
1               5                   10

<210> SEQ ID NO 4
<211> LENGTH: 4
<212> TYPE: PRT
<213> ORGANISM: Artificial Sequence
<220> FEATURE:
<223> OTHER INFORMATION: Synthetic peptide

<400> SEQUENCE: 4

Lys Val Val Asn
1

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide

<400> SEQUENCE: 5

Lys Val Val Asn
1
```

BIOACTIVE PEPTIDES AND COMPOSITIONS COMPRISING THEM

CROSS-REFERENCE TO RELATED APPLICATIONS

This application is a 371 of PCT/IB2020/055291, filed Jun. 5, 2020, which claims the benefit of Italian Patent Application No. 102019000008364, filed Jun. 7, 2019.

FIELD OF THE INVENTION

The present invention generally refers to the cosmeceutical field. More precisely, this invention relates to bioactive peptides and to cosmeceutical compositions comprising them, as well as to a cosmetic method comprising applying on a subject's skin this composition in order to prevent or treat the signs of skin aging, such as wrinkles and fine lines, loss of cutaneous elasticity and firmness. The present invention also relates to pharmaceutical compositions comprising the bioactive peptides for use in the treatment of pathologies to which are associated defects in the turnover of the dermal collagen, and in the post-cosmetic surgery treatment.

STATE OF THE ART

Synthetic peptides are known as a class of active ingredients of ever-increasing interest in the field of pharmaceutical and cosmeceutical technologies, where "cosmeceutics" means that branch of cosmetics, developed in recent years, which processes and produces formulations using the methods and criteria that are specific to pharmaceutical sciences.

Among the most popular products in this field, there are anti-aging formulations based on bioactive peptides acting on the turn-over mechanism of the dermal collagen, which with advancing age undergoes a slowdown thus creating a lack of collagen in the dermal layer and consequent loss of firmness and elasticity of the skin. The signs of aging (loss of elasticity, wrinkles, accentuation of expression lines, etc.) are accentuated too. Besides physiological causes related to advancing age, the lack of dermal collagen can also occur because of pathological causes. These bioactive peptides can work both by stimulating the biosynthesis of collagen and by inhibiting its degradation, thus making up for the lack of dermal collagen due to both physiological and pathological causes.

This situation can be corrected by active compounds capable of blocking or slowing down the intra-dermal degradation of collagen with suitable inhibitors: in this way, the dermal concentration of native collagen is increased, without intervening on the delicate biosynthesis processes carried out by fibroblasts. The inhibition of collagen degradation rather than the stimulation of its biosynthesis is therefore the preferred route of action for an active ingredient in this kind of formulations.

Collagen degradation is known to be regulated by two families of enzymes, namely the Matrix Metal Proteases (MMPs) and the serine proteases, but until today almost exclusively the MMP family has been considered as the target of enzymatic inhibitors having cosmeceutical interest, in order to prevent or treat the signs of skin aging by controlling the degradation of dermal collagen.

As far as serine proteases are concerned, the inventors have carried out studies on the pharmacological modulation of the collagen turnover using a serine protease inhibitor called Serpin A1 and fragments of its C-terminal region. In the paper by Cipriani C. et al., *Cell. Biol. International* (2018) 42: 1340-1348, the inventors had specifically evaluated the activity on collagen modulation of a C-terminal peptide fragment 409-418 of the serpin A1 molecule, termed SA1-III, in comparison with the activity of the same serpin A1, already described by other authors as capable of increasing the collagen production (see for example Dabbagh et al., *J. Cell. Physiol.* (2001) 186: 73-81).

In the above-mentioned paper, inventors reported increased levels of extracellular collagen in fibroblasts obtained from subjects of various ages by means of treatment with the previously mentioned fragment SA1-III that generates a reduction in the degradation of collagen.

The increased aging of the population and the ever-increasing attention of people to a pleasant and healthy aesthetic aspect makes highly felt the need for further and more active cosmeceutical products based on active peptides. These peptides are required to act effectively as inhibitors of serine-proteases against the signs of skin aging, exerting an effective protective action of the dermal collagen without causing cell proliferation effects.

SUMMARY OF THE INVENTION

Now the Applicants have synthesised novel peptides having a surprisingly high inhibitory activity of serine proteases, useful for the preparation of cosmeceutical compositions, for the prevention and treatment of the signs of cutaneous aging of the skin, and for the preparation of pharmaceutical compositions for post cosmetic surgery treatments.

Besides having an inhibitory activity towards the degradation of the dermal collagen surprisingly higher than Serpin A1 too and fragments thereof previously identified by the inventors, the present bioactive peptides have not shown undesirable effects of cellular proliferation. They are moreover short-length chain peptides, which can be easily synthesised also on a large scale at industrial level.

Furthermore, the novel bioactive peptides of the invention have shown a high protective efficacy towards collagen in in vitro tests, carried out by inventors and described in the following, on fibroblasts coming from young subjects and from old subjects too. This proves that they are useful for both the physiological skin aging conditions and the cutaneous aging signs due to pathologies in young subjects too, wherein the dermal collagen degradation rate exceeds the ability of the subjects to synthesise it.

Subjects of the present invention are therefore novel bioactive peptides of formula (I), whose essential characteristics are defined in the first of the attached claims. Further subject of this invention is a process for the preparation of the peptides, a cosmeceutical or pharmaceutical composition that comprises at least one of the above said peptides, and a cosmetic method comprising applying on the skin a composition, whose essential characteristics are defined respectively by the claims 6, 7, 11 and 10 here attached.

Further important characteristics of the peptides, of the process for their preparation, of the compositions comprising them, and of the cosmetic method according to the invention are subject of the dependent claims and illustrated in the following detailed description.

BRIEF DESCRIPTION OF THE FIGURES

FIG. 1 shows a histogram representing the concentration of Type I procollagen detected on cellular samples of fibroblasts treated with different products and in parallel with a peptide of this invention, as described in detail in the following examples.

DETAILED DESCRIPTION OF THE INVENTION

In the present invention, the terms "cosmetic composition" and "cosmeceutical composition" are indifferently used to mean a composition that has been formulated and manufactured by using the methods typical of the pharmaceutical preparations.

The bioactive peptides derivatives of the present invention are tetrapeptides, consisting of amino acids of the D series only, having the following general formula (I):

X-DAsn-DVal-DVal-DLys-Y  (I)

wherein:

X is an acyl group —CO—$(CH_2)_n CH_3$ linked to the N-terminus of asparagine, wherein n is an integer ranging between 0 and 20, and Y represents a —OH group at the C-terminus of lysine, or it is an amine group —$NR_1R_2$ linked to the C-terminus of lysine, wherein $R_1$ and $R_2$, equal or different to each other, are selected from between H and an alkyl group —$(CH_2)_m CH_3$ wherein m is an integer ranging between 0 and 2.

They are therefore tetrapeptides having the sequence of D amino acids shown above in the general formula (I), acylated at the N-terminus of the amino acid asparagine and optionally amidated at the C-terminus of the lysine.

According to a preferred embodiment of the invention, when Y is —$NR_1R_2$, then $R_1$ and $R_2$ are both H.

In a particular embodiment of the present invention, the present peptide has the above said formula (I) wherein n is an integer selected from 0 and 14, therefore X is respectively acetyl (indicated below also with the symbol "Ac") or palmitoyl.

Preferred according to the invention are the following tetrapeptide derivatives:

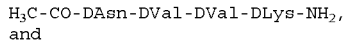

(SEQ ID NO: 1)
$H_3C$-CO-DAsn-DVal-DVal-DLys-$NH_2$,
and

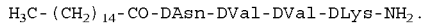

(SEQ ID NO: 2)
$H_3C$-$(CH_2)_{14}$-CO-DAsn-DVal-DVal-DLys-$NH_2$.

The peptide derivatives subject of this invention can be prepared by synthesis. For instance they can be prepared by peptide synthesis on solid phase, wherein the single amino acids of the peptide, in the same order of their position in formula (I), are added and attached to a first amino acid immobilised on a solid support, for example on a suitably functionalised resin. Then they are suitably acylated at the N-terminus before detachment from the resin. The peptides of the present invention can be advantageously prepared by using a strategy 9-fluorenyl-methoxycarbonyl/tert-butyl (Fmoc/tBu), such as that described in detail in the following experimental part.

Inventors have found that the peptides of the invention, and in particular Ac-DAsn-DVal-DVal-DLys-$NH_2$ (SEQ ID NO:1), have a surprising activity of protection against degradation of the dermal collagen. Furthermore, they have higher stability in vivo, thus being able to guarantee their protective effect on collagen for a prolonged period. They are therefore particularly useful as active principles in cosmetic or cosmeceutical compositions. Subject of this invention are therefore also those compositions comprising at least a peptide of formula (I) as defined above, together with one or more cosmetically acceptable excipients, adjuvants or carriers. The amount of peptide of formula (I) present in the composition can be for example comprised between 0.01 and 1% by weight with respect to the total weight of the composition, and it can be accompanied by one or more further cosmetically active principles. Examples of cosmetically acceptable excipients, adjuvants or carriers can be selected amongst perfumes, colouring agents, wetting/moisturizing agents, preservatives, functional and/or claim ingredients, solvents, and mixtures thereof. In an aspect of the present invention, the present compositions are formulated for the topical administration, for example in the form of serum, gel, lotion, ointment, cream or mousse.

Any person with ordinary technical skills in the field could easily and without efforts select the excipients, adjuvants and/or carriers most suitable to formulate the peptide composition of the invention to obtain the desired final form. The optimal conditions of preparation of uniform and stable compositions could be established as well. The thus prepared, present compositions can be packed in jar containers or can be distributed by means of pump dispensers, typically used for cosmetic lotions and gels.

Subject of this invention is moreover a cosmetic method for the prevention and treatment of the cutaneous ageing of skin, such as wrinkles, fine lines, loss of firmness and elasticity of the skin, comprising applying on the skin of a subject in need thereof the present cosmetic composition.

The peptides of this invention, for their properties towards dermal collagen, can furthermore find application also as active principles in pharmaceutical compositions useful in treatments following aesthetic surgery, where it is required a stimulation of the collagen production or a protection against degradation of the dermal collagen, for example after thread lifting treatments, or similar. Subject of this invention are therefore also such pharmaceutical compositions comprising at least a peptide of formula (I) as defined above, together with one or more pharmaceutically acceptable excipients, adjuvants or carriers; and the same compositions for use in the stimulation of the production of collagen or in the protection against collagen degradation in treatments following aesthetic surgery.

The cosmetic compositions and the pharmaceutical compositions of this invention ca comprise, besides at least an active peptide of formula (I), also one or more further ingredients having respectively cosmetic and/or pharmaceutical/dermatological activity.

As shown below in the experimental part, the peptides of this invention are endowed with an inhibitory activity in the degradation of dermal collagen that is surprisingly higher also with respect to Serpin A1 and fragments thereof previously identified by the inventors. Furthermore, they have been proved without undesired effects of cellular proliferation, they only have a protective action on the dermal collagen. This action was proved to be efficacious both on cells coming from old subjects, and also on cells coming from young subjects, thus showing a usefulness of the present peptides towards the physiological skin ageing conditions, but also promising good protective results also in the case of an excessive degradation rate of the dermal collagen with respect to the capacities of the subject of synthesising new collagen because of pathological conditions.

The present peptides are moreover tetrapeptides, therefore they are short-chain peptides, easier to synthesise, also on a large scale in industry.

The experimental part that follows is provided as an illustrative, non-limiting, example of the present invention.

Experimental Part

Synthesis of the Peptide Ac-DAsn-DVal-DVal-DLys-NH$_2$ (SEQ ID NO. 1)

The peptide of the title according to the invention, also indicated in the following and in FIG. 1 with the code AAT11RI, has been prepared by Solid-Phase Peptide Synthesis (SPPS) in a manual way, using a resin Rink-Amide AM and the 9-fluorenyl-methoxycarbonyl/tert-butyl strategy (Fmoc/tBu). After the attachment of the final amino acid to the resin, the peptide was acetylated at the N-terminus with acetic anhydride, then detached from the solid support with a mixture of TFA:H$_2$O:TIS:EDT (94:2.5:1:2.5).

The so obtained raw peptide was purified by semi-preparative RP-HPLC chromatography, to obtain a chromatographic purity of 98%, and then freeze-dried. Finally, the so obtained purified peptide of the title was characterised by analytical HPLC chromatography and by electrospray ionization mass spectrometry (ESI-MS).

Cell Cultures

Neonatal human dermal fibroblasts (NHDF) have been obtained from Lonza. Cultures of adult dermal fibroblasts have been prepared from cutaneous skin biopsies of healthy donors having different ages, as described in Pani et al. *J. Alzheimer's Dis.* (2009) 18:829-41, C6 (36-year-old men), C3 (57-year-old woman) and C12 (84-year-old woman). A written informed consent to use these dermal cells was obtained from all the donor subjects involved, according to the Guidelines indicated by the Ethics Committee of the Careggi University Hospital (Florence, Italy) and by the Helsinki Declaration of 1975, as reviewed in the 1983. All cell cultures have been subjected to a similar number of steps, from 6 to 9, at the beginning of the experiments, and were preserved in the modified Dulbecco Eagle culture medium (DMEM, Lonza) added with FBS 10% (Gibco), 100 units/ml of penicillin G, 0.05 mg/ml of streptomycin and glutamine 2 mM (PAN-Biotech GmbH), at 37° C. in a humidified incubator containing 5% of $CO_2$.

The cells were seeded in 12-wells plates (30000 cells per well) and treated the day after with the peptide AAT11RI (20 mM). In parallel the same cells were treated with TGF-β1 (10 ng/mL) and with the peptide SA1III (SEQ ID No: 3), which is the peptide previously described in Cipriani C. et al., *Cell. Biol. International* (2018) 42:1340-1348, as positive controls. The same cells were furthermore treated also with comparison peptides, not part of the invention, Peptide 1 (Ac-Lys-Val-Val-Asn-NH$_2$-SEQ ID No: 4), and Peptide 2 (Ac-DLys-DVal-DVal-DAsn-NH$_2$— SEQ ID No: 5).

All treatments have been carried out in the absence of FBS to avoid interferences in the electrophoretic migration. After 72 hours of incubation, the culture media have been collected, centrifuged at 250×g for 5 minutes; the supernatants were aliquoted and stored at −20° C. for analysis of collagen and zymography. The cellular proteins have been extracted in a RIPA buffer containing 1% of a mixture of inhibitors of proteases and phosphatases (Sigma-Aldrich Chemicals) with the help of a cell scraper. Cell lysates were then sonicated, purified by centrifugation and supernatants collected and stored at −20° C. The protein content in the lysates was measured using the Bio-Rad DC protein assay kit.

Test of Cells Viability

Cell viability assays were performed with the MTS cell proliferation tests in 96-well microplates (8,000 cells per well) after 72 hours of the treatments described above, following the instructions of the test manufacturer (Promega). All cell cultures have maintained their initial viability after the treatments.

Analisi Western Blot 30-40 µg of protein lysates obtained as described above for each cell sample have been subjected to electrophoretic separation on polyacrylamide gel with 4-12% of sodium dodecyl sulphate (Bis-Tris Plus BOLT, Invitrogen) under standard denaturation and reduction conditions, then they have been transferred onto polyvinylidene fluoride membranes (PVDF, Millipore). Collagen I and GAPDH proteins (the latter used as load control) have been determined by immunohistochemical method with primary polyclonal rabbit antibodies: anti-collagen type I, ab34710, Abcam; anti-GAPDH, 14C10 (Cell Signaling Technology) and with suitable secondary antibodies conjugated to peroxidase (Sigma-Aldrich Chemicals). The protein bands were visualized by using an enhanced chemiluminescence procedure with the Immobilon™ substrate of horseradish peroxidase (Millipore) and the immuno-reactive bands were quantified by densitometric analysis with Quantity-One software (Bio-Rad). Each density measurement was normalized by using the corresponding GAPDH level as an internal control.

For the measurement of type I soluble collagen in the culture media, 500 µl of each sample have been concentrated for 10 times with centrifuge filters having a cut-off from 3 to 30 K (Amicon Ultra-0.5 ml, Millipore). Approximately 20 µl of each sample have been then used for the Western Blot analysis. Each density measurement was normalised by the protein content of the cells in the corresponding well. As a reference control, in some experiments, type I human collagen (BD Bioscience) has been used together with the experimental samples under investigation. The markers used were Magic Mark (Invitrogen, visible in chemiluminescence) and Page Ruler (Thermo Scientific, visible at light).

FIG. 1 is a histogram showing the average of the type I procollagen concentrations detected in cell cultures with the various treatments described above and with a control that is a sample of untreated fibroblasts, according to the procedure described above.

It can be observed from these data that the tetrapeptide of the invention AAT11RI has an ability surprisingly higher than all the other products tested to increase the concentration of procollagen in vitro, also compared to the products used as a positive control as they are already known for their activity of collagen modulation. Moreover, the ability of the present peptides has revealed itself at relatively low concentrations, thus reflecting the high efficacy of the peptide.

Furthermore, the inventors have detected the same positive effect of the peptide of the invention for the cell cultures of neonatal fibroblasts as well as for the cultures of cells obtained from both adults and old subjects. Therefore the tested peptide has shown its usefulness in the treatment of different conditions of skin ageing, both physiological conditions due to the age of subject and pathological conditions caused by diseases having the skin ageing as a secondary effect because of the reduced capacity of the cells to produce collagen.

All values measured and reported in the graph of FIG. 1 are expressed as average±standard error. Statistical analyses have been carried out by using the one-way ANOVA test with Bonferroni post-hoc. The Student's t test was used for analysis of paired data. $p \leq 0.05$ was considered as a statistically significant difference.

The present invention was described above with reference to preferred embodiments thereof. It is to be understood that other embodiments may exist which belong to the same inventive core, as defined by the scope of the protection of the claims set forth below.

The invention claimed is:

1. A peptide derivative having formula (I)

$$\text{X-DAsn-DVal-DVal-DLys-Y} \quad (I)$$

wherein:
X is an acyl group —CO—$(CH_2)_n CH_3$ linked to the Asparagine N-terminus, wherein n is 14, and
Y is the —OH at the Lysine C-terminus, or it is an amino group —$NR_1R_2$ linked to the Lysine C-terminus, wherein $R_1$ and $R_2$, are selected from between H and an alkyl group —$(CH_2)_m CH_3$ wherein m is an integer comprised between 0 and 2.

2. The peptide derivative of claim 1, having general formula (I) wherein, when Y is —$NR_1R_2$, $R_1$ and $R_2$ are both H.

3. The peptide derivative of claim 1, which is $H_3C$—$(CH_2)_{14}$—CO-DAsn-DVal-DVal-DLys-$NH_2$ (SEQ ID NO:2).

4. A cosmetic composition comprising a peptide derivative of general formula (I) as defined in claim 1, and one or more cosmetically acceptable excipients, adjuvants or carriers.

5. The cosmetic composition of claim 4, wherein said cosmetically acceptable excipients, adjuvants or carriers are selected from the group consisting of perfumes, colouring agents, wetting/moisturising agents, preservatives, solvents, and mixtures thereof.

6. A pharmaceutical composition comprising the peptide derivative of general formula (I) as defined in claim 1, and one or more pharmaceutically acceptable excipients, adjuvants or carriers.

7. A process for the preparation of the peptide derivative as defined in claim 1, comprising a step of immobilizing a first amino acid on a solid support, followed by a step of adding each of the amino acids from the second to the fourth in the same order of general formula (I), and by a step of acylation at the Asn N-terminus, optionally followed by a step of amidation at the Lys C-terminus.

8. A cosmetic method for treating the signs of skin ageing in a subject comprising applying the cosmetic composition of claim 4 to the subject's skin.

9. A method of treating a subject's skin following cosmetic surgery, comprising applying the pharmaceutical composition of claim 6 to an area of the subject's skin after cosmetic surgery.

10. A method of treating a subject's skin following cosmetic surgery, comprising applying a pharmaceutical composition to the subject's skin, the composition comprising a peptide derivative having formula (I)

X-DAsn-DVal-DVal-DLys-Y (I)

wherein:
X is an acyl group —CO—$(CH_2)_n CH_3$ linked to the Asparagine N-terminus, wherein n is an integer comprised between 0 and 20, and Y is the —OH at the Lysine C-terminus, or it is an amino group —$NR_1R_2$ linked to the Lysine C-terminus, wherein $R_1$ and $R_2$, are selected from between H and an alkyl group —$(CH_2)_m CH_3$ wherein m is an integer comprised between 0 and 2.

11. The method of claim 10, wherein the pharmaceutical composition further comprises one or more pharmaceutically acceptable excipients, adjuvants or carriers.

* * * * *